US011339445B2

(12) United States Patent
Kim et al.

(10) Patent No.: US 11,339,445 B2
(45) Date of Patent: May 24, 2022

(54) METHOD FOR DETECTING TAC2 GENE SENSITIVE TO LOW-LEVEL IONIZING RADIATION, AND GENE DETECTED BY THE METHOD

(71) Applicant: KOREA HYDRO & NUCLEAR POWER CO., LTD, Gyeongju (KR)

(72) Inventors: Hee Sun Kim, Uijeongbu (KR); Seung Jin Choi, Seoul (KR); Moo Hyun Choi, Seoul (KR); Jin Jong Bong, Seoul (KR); Seok Cheol Shin, Seoul (KR)

(73) Assignee: KOREA HYDRO & NUCLEAR POWER CO., LTD, Gyeongju (KR)

( * ) Notice: Subject to any disclaimer, the term of this patent is extended or adjusted under 35 U.S.C. 154(b) by 781 days.

(21) Appl. No.: 16/193,901

(22) Filed: Nov. 16, 2018

(65) Prior Publication Data

US 2019/0085409 A1 Mar. 21, 2019

Related U.S. Application Data

(62) Division of application No. 14/399,953, filed as application No. PCT/KR2012/003906 on May 18, 2012, now Pat. No. 10,174,379.

(30) Foreign Application Priority Data

May 10, 2012 (KR) ........................ 10-2012-0049560

(51) Int. Cl.
    *C12Q 1/6886* (2018.01)
    *C12Q 1/6883* (2018.01)
(52) U.S. Cl.
    CPC ......... *C12Q 1/6886* (2013.01); *C12Q 1/6883* (2013.01); *C12Q 2600/106* (2013.01); *C12Q 2600/158* (2013.01)
(58) Field of Classification Search
    CPC ............................................. C12Q 2600/158
    See application file for complete search history.

(56) References Cited

FOREIGN PATENT DOCUMENTS

KR 10-0541529 B1 1/2006
KR 10-0957055 B1 5/2010

OTHER PUBLICATIONS

Gen Bank Accession No. XM_001472541.1, publicly available Jun. 2007, printed as pp. 1/1. (Year: 2007).*
Gen Bank Accession No. XM_001474025.3, publicly available February 2 012, printed as pp. 1/1. (Year: 2 012).*
Bong et al. Identification of the common radiation-sensitive and glucose metabolism-related expressed genes in the thymus of ICR and AKR/J mice. Proceedings of the Conference and Symposium Korean Association for Radiation Protection Fall Meeting 2011, pp. 86-87, Nov. 17, 2011. (Year: 2011).*
Shin et al. Life span and thymic lymphoma incidence in high- and low-dose-rate irradiated AKR/J mice and commonly expressed genes. Radiation Research, vol. 174, pp. 341-346, 2010. (Year: 2010).*
Taki et al. Microarray analysis of differentially expressed genes in the kidneys and testes of mice after long-term irradiation with low-dose-rate γ-rays. Journal of Radiation Research, vol. 50, No. 3, pp. 251-252, Apr. 2009. (Year: 2009).*
Gen Bank Accession No. BC031348.1, printed as pp. 1/2-2/2, publicly available Jul. 2006. (Year: 2006).*
Buck et al. Design strategies and performance of custom DNA sequencing primers. Biotechniques, vol. 27, No. 3, pp. 528-536, 1999. (Year: 1999).*
Eschrich et al., "Systems Biology Modeling of the Radiation Sensitivity Network: A Biomarker Discovery Platform," Inl. J. Radal. Oncol. Biol. Phys., Oct. 1, 2009, pp. 497-505, vol. 75, No. 2, Elsevier Inc.
Kabacik et al., "Gene expression following ionising radiation: Identification of biomarkers for dose estimation and prediction of individual response," Inl. J. Radial. Biol., Feb. 2011, pp. 115-129, vol. 87, No. 2, Informa UK, Lld.
Malone et al., "Novel Radiation Response Genes Identified in Gene-Trapped MCF10A Mammary Epithelial Cells," Radiation Research, 2007, pp. 176-184, vo. 167, Radiation Research Society.
Mezentsev et al., "Global Gene Expression Responses to Low- or High-Dose Radiation in a Human Three-Dimensional Tissue Model," Radial. Res., Jun. 2011, pp. 677-688, vol. 175, No. 6, Radiation Research Society.
NCBI GenBank Accession No. NM_011314.2, Feb. 15, 2015.
NCBI GenBank Accession No. NM_009312.2, Feb. 15, 2015.
NCBI GenBank Accession No. NM_020268.3, Feb. 15, 2015.
NCBI GenBank Accession No. NM_011260.1, Jan. 26, 2000.
NCBI GenBank Accession No. NM_054074.1, Nov. 12, 2001.
NCBI GenBank Accession No. NM_011314.1, Jan. 25, 2000.
NCBI GenBank Accession No. BC_01 9569.1, Oct. 19, 2006.
NCBI GenBank Accession No. BC_003878.1, Sep. 11, 2007.
NCBI GenBank Accession No. NM_011260.1, Feb. 15, 2015.
NCBI GenBank Accession No. NM_054074.1, Feb. 15, 2015.
Niu et al., "Radiation pharmacogenomics: A genome-wide association approach to identify radiation response biomarkers using human lymphoblastoid cell lines," Genome Research, 2010, pp. 1482-1492, vol. 20, Cold Spring Harbor Laboratory Press.
Ossetrova et al., "Multiple blood-proteins approach for eariy-response exposure assessment using an in vivo murine radiation model," Inl. J. Radial. Biol., Oct. 2009, pp. 837-850, vol. 85, No. 10, Informa UK Lld.

(Continued)

*Primary Examiner* — Jennifer Dunston

(57) ABSTRACT

A method for detecting genes sensitive to low-level ionizing radiation and genes detected by the method. More specifically, genes sensitive to low-level ionizing radiation and related to suppressing thymic cancer, discovered in a carcinogenic entity and verified in a normal entity are detected by subjecting a cancerous AKR/J mouse and a normal ICR mouse to low-level radiation. Thymus is collected therefrom, immunogenic and apoptotic genes are classified via microarray processing of the thymus. The genes are amplified and the levels of gene expression are measured. Thus, a gene having a specific reaction to radiation can be accurately detected by preventing the interference of confounding variables.

4 Claims, 2 Drawing Sheets

Specification includes a Sequence Listing.

(56) References Cited

OTHER PUBLICATIONS

Pogosova-Agadjanyan et al.. "Identification of Radiation-Induced Expression Changes in Nonimmortalized Human T Cells." Radial. Res., Feb. 2011, pp. 172-184, vol. 175, No. 2.
Shin et al., "Differential expression of immune-associated cancer regulatory genes in low-versus high-dose-rate irradiated AKR/J mice", Genomics, Jun. 2011, pp. 358-363, vol. 97, No. 6.
Turtoi et al., "Early gene expression in human lymphocytes after Y-irradiation—a genetic pattern with potential for biodosimetry," Inl. J. Radial. Biol., May 2008, pp. 375-387, vol. 84, No. 5, Informa UK Lld.

\* cited by examiner

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Ighg Forward Primer

<400> SEQUENCE: 1
gggctagacc tggatgatgt					20

<210> SEQ ID NO 2
<211> LENGTH: 20
<212> TYPE: DNA
<213> ORGANISM: Artificial Sequence
<220> FEATURE:
<223> OTHER INFORMATION: Ighg Backward Primer

<400> SEQUENCE: 2
gctgatgaag atggtgatgg					20

<210> SEQ ID NO 3
<211> LENGTH: 24
<212> TYPE: DNA
<213> ORGANISM: Artificial Sequence
<220> FEATURE:
<223> OTHER INFORMATION: Saa2 Forward Primer

<400> SEQUENCE: 3
agctggctgg aaagatggag acaa				24

<210> SEQ ID NO 4
<211> LENGTH: 24
<212> TYPE: DNA
<213> ORGANISM: Artificial Sequence
<220> FEATURE:
<223> OTHER INFORMATION: Saa2 Backward Primer

<400> SEQUENCE: 4
tgtcctctgc cgaagaattc ctga				24

<210> SEQ ID NO 5
<211> LENGTH: 20
<212> TYPE: DNA
<213> ORGANISM: Artificial Sequence
<220> FEATURE:
<223> OTHER INFORMATION: Reg3g Forward Primer

<400> SEQUENCE: 5
tcctgtcctc catgatcaaa					20

<210> SEQ ID NO 6
<211> LENGTH: 20
<212> TYPE: DNA
<213> ORGANISM: Artificial Sequence
<220> FEATURE:
<223> OTHER INFORMATION: Reg3g Backward Primer

<400> SEQUENCE: 6
acatcagcat tgctccactc					20

<210> SEQ ID NO 7
<211> LENGTH: 20
<212> TYPE: DNA
<213> ORGANISM: Artificial Sequence -continued

```
<220> FEATURE:
<223> OTHER INFORMATION: Defb6 Forward Primer

<400> SEQUENCE: 7
tggtgatgct gtctccactt                                               20

<210> SEQ ID NO 8
<211> LENGTH: 18
<212> TYPE: DNA
<213> ORGANISM: Artificial Sequence
<220> FEATURE:
<223> OTHER INFORMATION: Defb6 Backward Primer

<400> SEQUENCE: 8
catgaacgct ggcatgag                                                 18

<210> SEQ ID NO 9
<211> LENGTH: 20
<212> TYPE: DNA
<213> ORGANISM: Artificial Sequence
<220> FEATURE:
<223> OTHER INFORMATION: Tac2 Forward Primer

<400> SEQUENCE: 9
ggacttatgg gcaagaggaa                                               20

<210> SEQ ID NO 10
<211> LENGTH: 20
<212> TYPE: DNA
<213> ORGANISM: Artificial Sequence
<220> FEATURE:
<223> OTHER INFORMATION: Tac2 Backward Primer

<400> SEQUENCE: 10
gggattattt gaggatgcca                                               20

<210> SEQ ID NO 11
<211> LENGTH: 20
<212> TYPE: DNA
<213> ORGANISM: Artificial Sequence
<220> FEATURE:
<223> OTHER INFORMATION: Igh-VJ558 Forward Primer

<400> SEQUENCE: 11
gagaaatcct gagggagctg                                               20

<210> SEQ ID NO 12
<211> LENGTH: 20
<212> TYPE: DNA
<213> ORGANISM: Artificial Sequence
<220> FEATURE:
<223> OTHER INFORMATION: Igh-VJ558 Backward Primer

<400> SEQUENCE: 12
aggacgctgg acacactgta                                               20

<210> SEQ ID NO 13
<211> LENGTH: 19
<212> TYPE: DNA
<213> ORGANISM: Artificial Sequence
<220> FEATURE:
<223> OTHER INFORMATION: Klk1b27 Forward Primer

<400> SEQUENCE: 13
tgtaggagag acgggtgga                                                19
```

```
<210> SEQ ID NO 14
<211> LENGTH: 20
<212> TYPE: DNA
<213> ORGANISM: Artificial Sequence
<220> FEATURE:
<223> OTHER INFORMATION: Klk1b27 Backward Primer

<400> SEQUENCE: 14
taccgtggag aacaccatca                                              20
```

METHOD FOR DETECTING TAC2 GENE SENSITIVE TO LOW-LEVEL IONIZING RADIATION, AND GENE DETECTED BY THE METHOD

RELATED APPLLICATIONS

This application is divisional of U.S. patent application Ser. No. 14/399,953 filed Jan. 22, 2016, which is a § 371 application from PCT/KR2012/003906 filed May 18, 2012, which claims priority from Korean Patent Application No. 10-2012-0049560 filed May 10, 2012, each of which is herein incorporated by reference in its entirety.

REFERENCE TO ELECTRONIC SEQUENCE

The contents of electronic sequence listing (40X0447.txt; Size: 2.77 kilobytes; and Date of Creation: Nov. 15, 2018) is herein incorporated by reference in its entirety.

TECHNICAL FIELD

The present invention relates to a method for detecting genes sensitive to a low level of ionizing radiation and genes detected by the method, and more particularly, to a method for detecting genes sensitive to a low level of ionizing radiation, the method including irradiating cancer-induced mice and normal mice with a low level of radiation, and screening immunity-related and apoptosis-related genes, which are observed commonly in the normal mice and the cancer-induced mice, from the thymi of the mice.

BACKGROUND ART

With an increase in the industrial and medical use of radiation, various studies on the effects of radiation on the human body have been conducted, and particularly, cancer therapy with radiation has received attention. It is known that high doses of ionizing radiation cause DNA damage, genetic modification, and diseases, including cancer, but a radiation dose of 200 mGy or less and a radiation dose rate of mGy/hr or less inhibit cancer development by activating immune responses.

In general, studies on the relationship between radiation and cancer development, particularly gene responses to radiation, have been conducted, but confounding factors have significantly affected the results to reduce the reliability of the results. However, most studies conducted to date could not explain various responses, which occur in the cells, tissues and organs of the body in the body stage, because these studies were performed using gene-modified cell lines or cancer cell lines. In other words, because gene responses were evaluated using general mice, a variety of genes were expressed, and because cancer development was not limited to a specific organ, it was difficult to analyze gene responses.

In prior art methods that use cells for cancer research, genes were modified, or cancer cells lacking p53 that is important in cancer development were irradiated. For this reason, there was a problem in that the results could not be applied to individuals, because they did fundamentally differ from the responses of normal cells. To overcome this problem, studies on the effects of radiation on cancer development have been conducted using mice having a gene similarity of 95% or more with humans. However, cancer incidence in general mice is very low, and thus a variety of mouse models for cancer research have been used.

In prior studies, a variety of methods were used to screen genes sensitive to a low level (0.7 mGy/hr) of radiation. However, genes disclosed in the present invention are not yet known as genes sensitive to a low level (0.7 mGy/hr) of radiation. Technologies prior to the identification of the profile of genes according to the present invention are as follows.

(1) Radiation-sensitive genes were identified in human breast epithelial cells using a gene probe method (Malone J, Ullrich R (2007) Radiat Res 167: 176-1847).

(2) Genes sensitive to early radiation were found in irradiated human lymphocytes using microarray analysis and a quantitative nucleic acid amplification technique (Turtoi A et. al. (2008) Int J Radiat Biol 84: 375-387).

(3) Biological dose markers were identified in male BALB/c, irradiated with 1-7 Gy, by blood protein analysis (Ossetrova N I, Blakely W F (2009) Int J Radiat Biol 85: 837-850).

(5) A network of 10 herb genes including c-Jun, HDAC1, RELA (p65 subunit of NFKB), PKC-beta, SUMO-1, c-Abl, STAT1, AR, CDK1 and IRF1 was identified by linear regression analysis of 500 genes that represent a biological network (Eschrich S et. al. (2009) Int J Radiat Oncol Biol Phys 75: 497-505).

(5) Single nucleotide polymorphism markers enabling the prediction of response to radiation were identified in 277 human lymphocyte cell lines (Niu N et. al. (2010) Genome Res 20: 1482-1492).

(6) A recent study provided a new overview of response to radiation using EPI-200 that is a three-dimensional tissue model mimicking human epidermal tissue (Mezentsev A, Amundson S A (2011) Radiat Res 175: 677-688).

(7) An RNA-based expression analysis method was used as a tool for biological dose evaluation in the measurement of radiation exposure and toxicity (Pogosova-Agadjanyan E L et. al. (2011) Radiat Res 175: 172-184).

(8) Radiation-sensitive genes were identified in human lymphocytes and leucocytes using multiplex quantitative nucleic acid amplification and a method for analysis of a specific gene (Kabacik S et. al. (2011) Int J Radiat Biol 87: 115-129).

Accordingly, the present inventors have made efforts to find genes showing a sensitive response to a low level of ionizing radiation. As a result, the present inventors have analyzed the functions of 7 genes playing an important role in immunity (Ighg, Saa2, Defb6, Reg3g, Tac2 and Igh-VJ558) and apoptosis (Klk1b27), and have found that the seven genes have not been reported, thereby completing the present invention.

DISCLOSURE

Technical Problem

It is an object of the present invention to a method for detecting a gene sensitive to a low level of ionizing radiation, and a gene detected by the method.

Technical Solution

In order to accomplish the above object, the present invention provides a method for detecting a gene, which is sensitive to a low level of radiation, identified in a cancer-induced individual, verified using a normal individual, and involved in suppression of thymic cancer, the method including the steps of: I) irradiating a cancer-induced AKR/J mouse and a normal ICR mouse with a low level of radiation; II) extracting thymi from the AKR/J mouse and the ICR mouse; III) analyzing the thymi by microarray analysis; IV) selecting an immunity-related or apoptosis-related gene from the microarray analysis through Venn diagram analysis; and V) amplifying the gene and measuring the expression level of the gene.

The present invention also provides a marker for diagnosing the suppression of thymic cancer, the marker including either an immunity-related gene selected from the group consisting of Ighg (XM_001472541), Saa2 (NM_011314), Reg3g (NM_011260), Defb6 (NM_054074), Tac2 (NM_009312) and Igh-VJ558 (XM_001474025), which are involved in the suppression of thymic cancer, or an apoptosis-related gene Klklb27 (NM_020268).

The present invention also provides a kit for diagnosing the suppression of thymic cancer, the kit including the above marker.

The present invention also provides a microarray for diagnosing thymic cancer, the microarray including the above marker.

The present invention also provides a method for detecting a gene for treating or suppressing thymic cancer, the method including the steps of: I) irradiating a mammal having thymic cancer with radiation; II) bringing a test substance into contact with a thymic tissue extracted from the irradiated mammal; and III) measuring, from the thymic tissue, a change in the expression of either an immunity-related gene selected from the group consisting of Ighg (XM_001472541), Saa2 (NM_011314), Reg3g (NM_011260), Defb6 (NM_054074), Tac2 (NM_009312) and Igh-VJ558 (XM_001474025), which are involved in suppression of thymic cancer, or an apoptosis-related gene Klklb27 (NM_020268).

Hereinafter, the present invention will be described in detail.

According to the present invention, Ighg and Igh-VJ558, known to be involved in immune responses, were activated by a low level of radiation. It was found that a low level of radiation can activate an immune response during the development of thymic cancer.

Also, it was analyzed that Saa2 is involved in a systemic inflammatory response and the production of free fatty acids (Lopez-Nieva P et. al. (2004) Carcinogenesis 25: 1299-1304). In addition, it was analyzed that Reg3g is involved in an inflammatory response (Beverly L J, Felsher D W (2005) Cancer Res 65: 7159-7168), and that Defb6 is involved in an immune response in genitourinary organs (Yamaguchi Y et. al. (2002) J Immunol 169: 2516-2523).

Moreover, it was analyzed that Tac2 is observed mainly in neuronal cells and non-neuronal cells and involved in the synthesis of gonadotropin in males (Corander M P et. al. (2010) J Neuroendocrinol 22:181-187). In addition, it was analyzed that Klklb27 is serine protease and involved in insulin growth hormone protein binding (REACTOME: 1494374).

Many studies on the effects of radiation on cancer development among the effects of radiation on the human body have been conducted, but it was difficult to explain various responses of the body to radiation (responses of genes to radiation), because these studies were performed using cancer cells, gene-modified cell lines or general mice. Particularly, the profile of genes sensitive to a low level (0.7 mGy/hr) of radiation in individuals has not yet been identified, and the functions of these genes have not been explained. Accordingly, the present invention is intended to (1) identify the profile of genes that are expressed specifically in thymus and sensitive to a low level of radiation, and analyze the functions of the genes, after irradiating a low level (0.7 mGy/hr) of radiation (cancer development stimulator) to normal ICR mice and AKR/J mice that develop thymic cancer, and 2) diagnose the stage of development of thymic cancer using the profile of genes.

The present invention provides a method for detecting a gene, which is identified in a cancer-induced individual, is verified using a normal individual, and is involved in suppression of thymic cancer, the method including the steps of: I) irradiating a cancer-induced AKR/J mouse and a normal ICR mouse with a low level of radiation; II) extracting thymi from the AKR/J mouse and the ICR mouse; III) analyzing the thymi by microarray analysis; IV) selecting an immunity- or apoptosis-related gene from the microarray analysis through Venn diagram analysis; and V) amplifying the gene and measuring the expression level of the gene.

In the inventive method for detecting a gene sensitive to a low level of ionizing radiation, irradiating the mice with the low level of radiation is preferably performed by irradiating gamma radiation (Cs-137) at a dose rate of 0.7 mGy/hr to a final dose of 1.7 Gy. The method according to the present invention is preferably used for preparation of a kit for diagnosing thymic cancer, evaluation of the degrees of progression and treatment of cancer in a cancer patient, evaluation of the relationship between radiation exposure of industrial and medical workers and cancer development, evaluation of the causal relation between radiation and cancer development, biological evaluation of radiation exposure dose, or evaluation of the degrees of development and progression of thymic cancer caused by a low level of radiation.

In addition, the inventive method for detecting a gene sensitive to a low level of ionizing radiation, the cancer is preferably thymic cancer, and extracting the thymi in step II) is preferably performed at a time point when the mouse starts to die of the cancer.

Furthermore, in the inventive method for detecting a gene sensitive to a low level of ionizing radiation, the immunity-related gene is preferably selected from the group consisting of Ighg (XM_001472541), Saa2 (NM_011314), Reg3g (NM_011260), Defb6 (NM_054074), Tac2 (NM_009312) and Igh-VJ558 (XM_001474025), and the apoptosis-related gene is preferably Klklb27 (NM_020268). Preferably, the Ighg (XM_001472541) gene is amplified using primers having sequences set forth in SEQ ID NOS: 1 and 2; the Saa2 (NM_011314) gene is amplified using primers having sequences set forth in SEQ ID NOS: 3 and 4; the Reg3g (NM_011260) gene is amplified using primers having sequences set forth in SEQ ID NOS: 5 and 6; the Defb6 (NM_054074) gene is amplified using primers having sequences set forth in SEQ ID NOS: 7 and 8; the Tac2 (NM_009312) gene is amplified using primers having sequences set forth in SEQ ID NOS: 9 and 10; the Igh-VJ558 (XM_001474025) gene is amplified using primers having sequences set forth in SEQ ID NOS: 11 and 12; and the Klklb27 (NM_020268) gene is amplified using primers having sequences set forth in SEQ ID NOS: 13 and 14.

In step IV) of selecting the related gene from the microarray analysis, a gene overexpressed in the cancer-induced individual after irradiation compared to in the cancer-induced individual before irradiation is detected by microarray analysis, and thus verified using primers having sequences of two of SEQ ID NOS: 1 to 10, and the overexpressed or underexpressed gene is identified by performing a search for the function thereof. The microarray analysis is described in the Examples below, and the overexpressed gene is identified by performing a search for the function thereof. The microarray analysis is described in the Examples below, and verification is performed using primers having sequences of SEQ ID NOS: 1 to 14. A search for the function of the gene was performed in the Examples through BioCarta (www.biocarta.com/), GenMAPP (www.genmapp.org/), the DAVID bioinformatics database (appsl.niaid.nih.gov) and the Pubmed database (www.ncbi.nlm.nih.gov), but is not limited thereto.

As used herein, "gene sensitive to a low level of radiation" refers to a gene that is differentially overexpressed in a cancer-induced individual after radiation compared to before irradiation. In other words, the gene refers to a gene whose expression pattern is changed by stimulation with radiation, and it may be a target gene associated with a specific cancer, that is, an oncogene or a tumor suppressor gene. When this cancer-specific gene is detected, a molecular mechanism for radiotherapy of cancer patients can be established, which can contribute to an increase in the effect of radiotherapy, and a platform for the development of agents or methods for treating cancer at the biomolecular level can be provided by screening novel oncogenes or tumor suppressor genes and regulating the expression thereof.

The present invention also provides a marker for diagnosing the suppression of thymic cancer, the marker including either an immunity-related gene selected from the group consisting of Ighg (XM_001472541), Saa2 (NM_011314), Reg3g (NM_011260), Defb6 (NM_054074), Tac2 (NM_009312) and Igh-VJ558 (XM_001474025), which are involved in the suppression of thymic cancer, or an apoptosis-related gene Klklb27 (NM_020268).

The present invention also provides a kit for diagnosing the suppression of thymic cancer, the kit including the above marker.

The present invention also provides a microarray for diagnosing thymic cancer, the microarray including the above marker.

The present invention also provides a method for detecting a gene for treating or suppressing thymic cancer, the method including the steps of: I) irradiating a mammal having thymic cancer with radiation; II) bringing a test substance into contact with a thymic tissue extracted from the irradiated mammal; and III) measuring, from the thymic tissue, a change in the expression of either an immunity-related gene selected from the group consisting of Ighg (XM_001472541), Saa2 (NM_011314), Reg3g (NM_011260), Defb6 (NM_054074), Tac2 (NM_009312) and Igh-VJ558 (XM_001474025), which are involved in suppression of thymic cancer, or an apoptosis-related gene Klklb27 (NM_020268).

In the present invention, AKR/J mice (models for thymic cancer research) and healthy ICR mice were irradiated with a low level (0.7 mGy/hr) of gamma radiation (Cs-137), and thymi were extracted at a time point (day 100) when the AKR/J mice started to die of thymic cancer. The extracted thymi were analyzed by microarray analysis, and then immunity- and apoptosis-related genes that responded sensitively to the low level of radiation (0.7 mGy/hr) were selected through Venn diagram analysis, and subjected to nucleic acid amplification, and the expression levels thereof were measured.

As a result, 7 genes, including immunity-related genes (Ighg, Saa2, Defb6, Reg3g, Tac2 and Igh-VJ558) and an apoptosis-related gene (Klk1b27), which responded sensitively to the low level (0.7 mGy/hr) of radiation, were screened in the present invention. Also, it was found that a low level (0.7 mGy/hr) of radiation suppressed thymic cancer by activating immunity-related genes (Ighg, Saa2, Defb6, Reg3g, Tac2 and Igh-VJ558) and an apoptosis-related gene (Klk1b27) in thymocytes. As described above, according to the present invention, the functions of the related genes were suggested, and the responses of glucose metabolism-related genes to a low level of radiation could be consistently observed by extracting thymi at day 100 when death caused by thymic cancer was observed.

Therefore, the present invention may be used to: (1) identify the profile of genes for development of a kit for diagnosing thymic cancer; (2) identify a marker for evaluating the relation of cause and effect of cancer development in industrial and medical workers who live in environments having a low level of radiation; (3) identify the profile of genes for information, which enable the diagnosis of cancer development in cancer patients and allow a cancer therapeutic method to be established; (4) identify a marker for evaluating the causal relation between radiation exposure and the development of thymic cancer; 5) identify a novel gene marker that may be widely used for biological evaluation of a low level of radiation exposure; and (6) understand ionizing radiation-sensitive glucose metabolism signaling that may be used as a target therapy for a low level of radiation exposure.

Advantageous Effects

The method for detecting a gene sensitive to a low level of ionizing radiation as described above may be used to establish the profile of marker genes sensitive to a low level of radiation in order to prepare a kit for diagnosing thymic cancer, and may provide a marker gene sensitive to a low level of radiation, which can be used to evaluate the degrees of progression and progression of cancer in cancer patients. Also, the method according to the present invention may provide a marker gene sensitive to a low level of radiation, which can be used to evaluate the relationship between the radiation exposure of industrial and medical workers and cancer development. Further, it may provide a marker sensitive to a low level of radiation, which can be used to evaluate the causal relation between radiation and cancer development. In addition, it may provide a novel marker that can be used for biological evaluation of radiation exposure dose. Also, it may provide a gene marker sensitive to a low level of radiation (0.7 mGy/hr), which can be used to evaluate the low-level radiation on the suppression of thymic cancer.

MODE FOR INVENTION

Figure 1:
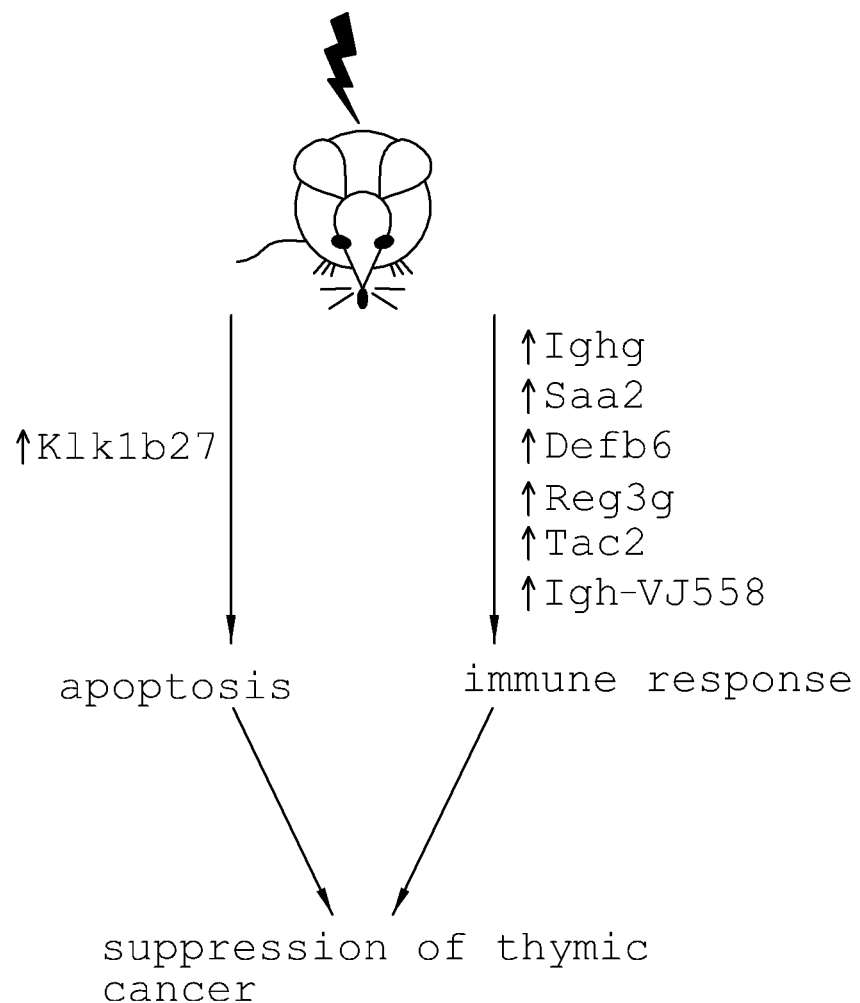
FIG. 1 schematically shows that a low level (0.7 mGy/hr) of radiation suppresses thymic cancer by activating immunity-related genes (Ighg, Saa2, Defb6, Reg3g, Tac2 and Igh-VJ558) and an apoptosis-related gene (Klk1b27) in thymocytes.

Hereinafter, the present invention will be described in further detail with reference to examples. It is to be understood, however, that these examples are for illustrative purposes only and are not intended to limit the scope of the present invention.

Example 1

6-Week-old female AKR/J mice (models for thymic cancer research) and 6-week-old female ICR mice were purchased from SLC Co., Ltd. (Japan). A low level of radiation ($^{137}$Cs) was irradiated to the AKR/J mice using a gamma-ray generator (IBL 147C, CIS bio international, France) at a dose rate of 0.7 mGy/hr so as to reach a final dose of 1.7 Gy. After completion of irradiation with the low level of radiation, the mice were transferred into a sterilized housing system shielded from radiation, and were housed therein for 100 days while the observation of development of thymic cancer was performed. For gene analysis, under the same experimental conditions, normal mice (ICR mice) housed separately from the AKR/J mice were irradiated with a low level of radiation (0.7 mGy/hr). After 100 days, thymi were extracted from the mice and frozen rapidly in liquid nitrogen, after which gene analysis was performed.

Example 2: Microarray and Gene Analysis

Using mouse models (AKR/J mice) for cancer research, irradiated in Example 1, genes sensitive to a low level of radiation (0.7 mGy/hr) were screened. The screened genes were verified using normal mice (ICR mice). Specifically, genes that responded to a low level of radiation (0.7 mGy/hr) specifically in the thymi of the AKR/J and ICR mice irradiated with the low-level of radiation (0.7 mGy/hr) were screened, and their functions were analyzed. Analysis was performed using Venn diagrams, a quantitative nucleic acid amplification technique, and the statistical program SAS (ANOVA and t-test).

To confirm the results, the genes were subjected to nucleic acid amplification. Specifically, the thymi extracted from the AKR/J and ICR mice irradiated with the low level of radiation (0.7 mGy/hr) were microarrayed, and genes that responded sensitively to the low level of radiation were amplified using the primers shown in Table 1 below in order to measure the expression levels thereof.

TABLE 1

| Gene No. | Gene name | Forward (5' → 3') | Reverse (5' → 3') |
|---|---|---|---|
| NM_001472541 | Ighg | GGGCTAGACCTGGA TGATGT (SEQ ID NO 1) | GCTGATGAAGATGG TGATGG (SEQ ID NO 2) |
| NM_011314 | Saa2 | AGCTGGCTGGAAAG ATGGAGACAA (SEQ ID NO 3) | TGTCCTCTGCCGAA GAATTCCTGA (SEQ ID NO 4) |
| NM_011260 | Reg3g | TCCTGTCCTCCATG ATCAAA (SEQ ID NO 5) | ACATCAGCATTGCT CCACTC (SEQ ID NO 6) |
| NM_054074 | Defb6 | TGGTGATGCTGTCT CCACTT (SEQ ID NO 7) | CATGAACGCTGGCA TGAG (SEQ ID NO 8) |
| NM_009312 | Tac2 | GGACTTATGGGCAA GAGGAA (SEQ ID NO 9) | GGGATTATTTGAGG ATGCCA (SEQ ID NO 10) |

TABLE 1-continued

| Gene No. | Gene name | Forward (5' → 3') | Reverse (5' → 3') |
|---|---|---|---|
| NM_001474025 | Igh-VJ558 | GAGAAATCCTGAGG GAGCTG (SEQ ID NO 11) | AGGACGCTGGACAC ACTGTA (SEQ ID NO 12) |
| NM_020268 | Klk1b27 | TGTAGGAGAGACGG GTGGA (SEQ ID NO 13) | TACCGTGGAGAACA CCATCA (SEQ ID NO 14) |

After irradiation of the AKR/J and ICR mice with the low level of radiation (0.7 mGy/hr), the mice were housed, and thymi were extracted from the mice at a time point (day 100) when the AKR/J mice started to die of thymic cancer. The extracted thymi were microarrayed, and genes that responded sensitively to the low level of radiation were selected, and then subjected to nucleic acid amplification, and the expression levels thereof were measured. As a result, it was shown that, in the mice irradiated with the low level of radiation, immunity-related genes (Ighg, Saa2, Defb6, Reg3g, Tac2 and Igh-VJ558) and an apoptosis-related gene (Klk1b27) responded sensitively to the low level of radiation. The results are shown in Table 2 below.

TABLE 2

|  |  | Microarray | | Quantitative nucleic acid amplification | |
|---|---|---|---|---|---|
| Gene No. | Gene name | ICR mice | AKR/J mice | ICR mice | AKR/J mice |
| XM_001472541 | Ighg | 17.2 | 2.2 | 42 ± 30* | 12 ± 8.7 |
| NM_011314 | Saa2 | 1.1 | 0.7 | 116 ± 45 | 27 ± 21 |
| NM_011260 | Reg3g | 0.9 | 0.9 | 1174 ± 959 | 11 ± 6.2 |
| NM_054074 | Defb6 | 1.3 | 0.6 | 47 ± 28 | 7.5 ± 4.6 |
| NM_009312 | Tac2 | 0.8 | 0.8 | 26 ± 10 | 6.9 ± 3.9 |
| XM_001474025 | Igh-VJ558 | 1.0 | 1.0 | 22 ± 17 | 6.8 ± 2.6 |
| NM_020268 | Klk1b27 | 0.6 | 2.5 | 1.9 ± 0.2 | 10 ± 3.6 |

*Expression fold value ± SD

FIG. 1 schematically shows that a low level (0.7 mGy/hr) of radiation suppressed thymic cancer by activating immunity-related genes (Ighg, Saa2, Defb6, Reg3g, Tac2 and Igh-VJ558) and an apoptosis-related gene (Klk1b27) in thymocytes.

Figure 2:
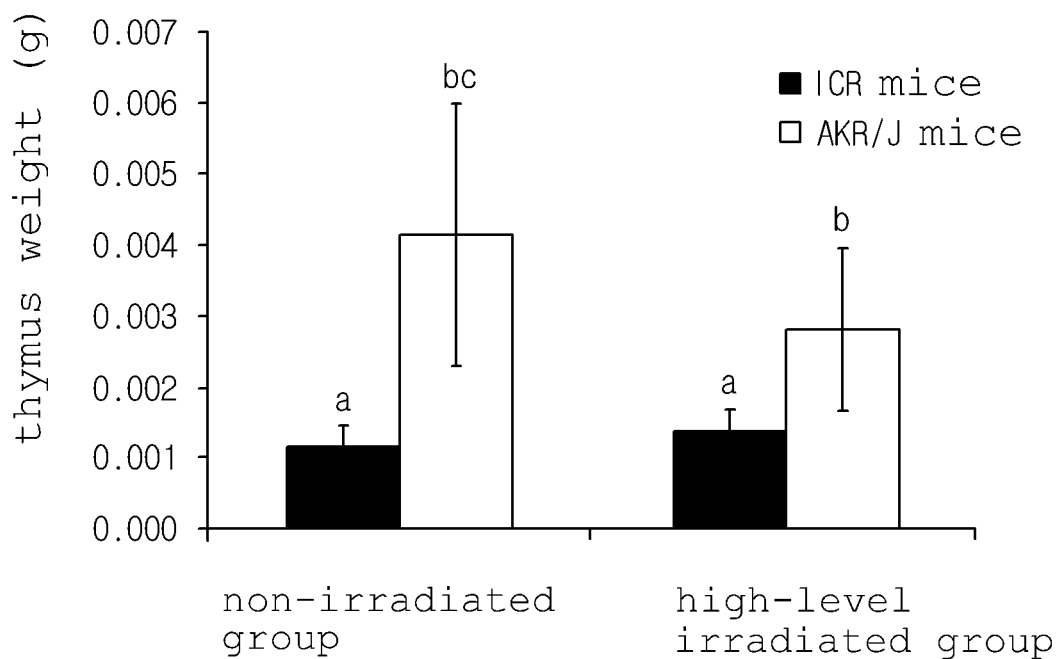
FIG. 2 is a graph showing the results obtained by irradiating AKR/J mice ICR mice with a low level (0.7 mGy/hr) of radiation and measuring the weight of thymi of the mice at a time point (day 100) when the mice started to die of thymic cancer during their housing, in order to analyze the responses of genes sensitive to radiation based on the thymus weight.

FIG. 2 is a graph showing the results obtained by irradiating AKR/J mice ICR mice with a low level (0.7 mGy/hr) of radiation and measuring the weight of thymi of the mice at a time point (day 100) when the mice started to die of thymic cancer during their housing, in order to analyze the responses of genes sensitive to radiation based on the thymus weight. According to the present invention, genes that respond sensitively to a low level of radiation can be consistently measured by extracting thymi in an early stage of cancer development in which mice start to die of thymic cancer, and comparing the weights of the extracted thymi.

The invention claimed is:

1. A method for detecting a gene sensitive to a radiation, the method comprising the steps of:
   irradiating a cancer-induced AKR/J mouse and an ICR mouse with a gamma radiation at a dose rate of 0.7 mGy/hr to a final dose of 1.7 Gy;
   extracting thymi from the AKR/J mouse and the ICR mouse;
   analyzing the thymi by a microarray analysis;
   selecting an immunity-related gene Tac2 from the microarray analysis through a Venn diagram analysis; and
   amplifying the gene and measuring an expression level of the gene.

2. The method of claim 1, wherein the cancer is thymic cancer.

3. The method of claim 1, further comprising the step of extracting the thymi at a time point when the mouse starts to die of the cancer.

4. The method of claim 1, wherein the step of amplifying the Tac2 gene uses primers having sequences set forth in SEQ ID NOS: 9 and 10.

* * * * *